(12) United States Patent
Goodman et al.

(10) Patent No.: US 11,987,562 B2
(45) Date of Patent: May 21, 2024

(54) PRODUCTION OF HYDROXYETHYLPIPERAZINE

(71) Applicant: Dow Global Technologies LLC, Midland, MI (US)

(72) Inventors: Amanda M. Goodman, Missouri City, TX (US); Jianping Zeng, Manvel, TX (US); Barry Archer, Lake Jackson, TX (US); Christophe R. Laroche, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 529 days.

(21) Appl. No.: 17/287,628

(22) PCT Filed: Oct. 23, 2019

(86) PCT No.: PCT/US2019/057612
§ 371 (c)(1),
(2) Date: Apr. 22, 2021

(87) PCT Pub. No.: WO2020/092082
PCT Pub. Date: May 7, 2020

(65) Prior Publication Data
US 2021/0395211 A1 Dec. 23, 2021

Related U.S. Application Data

(60) Provisional application No. 62/752,437, filed on Oct. 30, 2018.

(51) Int. Cl.
*C07D 295/088* (2006.01)
*B01D 3/00* (2006.01)
*B01D 3/14* (2006.01)

(52) U.S. Cl.
CPC ......... *C07D 295/088* (2013.01); *B01D 3/009* (2013.01); *B01D 3/143* (2013.01)

(58) Field of Classification Search
CPC ..... C07D 295/088; B01D 3/009; B01D 3/143
See application file for complete search history.

(56) References Cited

U.S. PATENT DOCUMENTS

| | | | |
|---|---|---|---|
| 3,639,403 A | 2/1972 | Muhlbauer | |
| 6,013,801 A | 1/2000 | Koll et al. | |
| 8,558,029 B2 | 10/2013 | Tirtowidjojo et al. | |
| 2008/0287479 A1 | 11/2008 | Hutchings et al. | |

FOREIGN PATENT DOCUMENTS

| | | |
|---|---|---|
| DE | 206670 A3 | 2/1984 |
| JP | 60043346 | 3/1985 |
| WO | 2017011283 | 1/2017 |

OTHER PUBLICATIONS

PCT/US2019/057612, International Search Report and Written Opinion with a mailing date of Jan. 20, 2020.
PCT/US2019/057612, International Preliminary Report on Patentability with a mailing date of Apr. 27, 2021.

*Primary Examiner* — Sikarl A Witherspoon

(57) ABSTRACT

Embodiments relate to a continuous process for the production of hydroxyethylpiperazine that includes feeding neat piperazine, recycled piperazine, and ethylene oxide to a reactor to form crude hydroxyethylpiperazine, in which the reactor is a continuous stirred tank reactor or a plug flow reactor. The process further includes continuously feeding the crude hydroxyethylpiperazine from the reactor to a distillation system that includes at least one distillation column, the distillation system produces at least a recycled piperazine stream and a hydroxyethylpiperazine stream, the recycled piperazine stream includes the recycled piperazine that is fed to the reactor to form the crude hydroxyethylpiperazine, and the hydroxyethylpiperazine stream includes at least 60 wt % of hydroxyethylpiperazine based on a total weight of the hydroxyethylpiperazine stream.

8 Claims, 2 Drawing Sheets

PRODUCTION OF HYDROXYETHYLPIPERAZINE

FIELD

Embodiments relate to a process for the preparation of hydroxyethylpiperazine and hydroxyethylpiperazine products prepared according to such a process.

INTRODUCTION

Piperazine ("PIP") is an organic compound that includes a six member ring containing two nitrogen atoms. Piperazine may be formed as a co-product in the ammoniation of 1,2-dichloroethane or ethanolamine. Hydroxyethylpiperazine ("HEP") is a piperazine that further includes a hydroxyethyl group, which may be referred to as 1-(2-hydroxyethyl) piperazine. For example, hydroxyethylpiperazine may have the following structure:

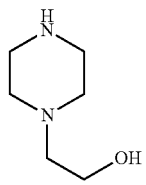

Hydroxyethylpiperazine may be formed by an ethoxylation reaction of piperazine (e.g., by the reaction of preformed piperazine with ethylene oxide). A process for manufacturing hydroxyethylpiperazine may produce both hydroxyethylpiperazine and dihydroxyethylpiperazine ("DiHEP"). The resultant product may be useful as a mixture or may utilize additional processing steps to purify the product streams to form a desired product. Also, this process may be modified to favor the production of one piperazine product over another piperazine product. For example, high molar ratios of ethylene oxide to piperazine may allow for the production of dihydroxyethylpiperazine to dominate and decrease yield of hydroxyethylpiperazine, which is disfavored when seeking to produce hydroxyethylpiperazine of high purity. Further, low molar ratios of ethylene oxide to piperazine may result in a significant amount of unreacted piperazine and separation of the unreacted piperazine at a commercial process scale may be difficult as piperazine solidifies at room temperature. As such, there is a need to utilize a process for the production of hydroxyethylpiperazine that allows for the continuous monitoring of the molar ratio of ethylene oxide to piperazine, so as to minimize these concerns associated with high and lower molar ratios of ethylene oxide to piperazine.

International Publication No. WO/2017/011283 discloses a process for producing hydroxy alkyl piperazine compounds that includes (i) feeding a feed stream of piperazine at a first location into a reactive distillation column, and (ii) feeding a feed stream of a $C_2$ to $C_8$ alkylene oxide at one or more second location into the reactive distillation column. While use of reactive distillation may favor the monohydroxyethyl piperazine and/or eliminate the need for a separate multistep distillation, alternative methods are sought that utilize standard equipment in a continuous process to further enable the ability to cost-effectively produce large quantities of hydroxyethylpiperazine at a commercial scale.

SUMMARY

Embodiments may be realized by a continuous process for the production of hydroxyethylpiperazine that includes feeding neat piperazine, recycled piperazine, and ethylene oxide to a reactor to form crude hydroxyethylpiperazine, in which the reactor is a continuous stirred tank reactor or a plug flow reactor. The process further includes continuously feeding the crude hydroxyethylpiperazine from the reactor to a distillation system that includes at least one distillation column, the distillation system produces at least a recycled piperazine stream and a hydroxyethylpiperazine stream, the recycled piperazine stream includes the recycled piperazine that is fed to the reactor to form the crude hydroxyethylpiperazine, and the hydroxyethylpiperazine stream includes at least 60 wt % of hydroxyethylpiperazine based on a total weight of the hydroxyethylpiperazine stream.

BRIEF DESCRIPTION OF THE DRAWINGS

Features of the embodiments will become more apparent to those of ordinary skill in the art by describing in detail exemplary embodiments thereof with reference to the attached drawings in which.

DETAILED DESCRIPTION

A continuous process for the production of hydroxyethylpiperazine (also referred to herewithin as HEP) is proposed that utilizes a recycled stream of piperazine to a reactor coupled with a distillation process that recycles piperazine back to the reactor after a separation process. The reactor is a continuous stirred tank reactor or a plug flow reactor. The continuous process would operate at a low molar ratio of ethylene oxide to piperazine in a reactor and recycle the unreacted piperazine back to the reactor. The continuous process with the reactor and recycle stream may unexpectedly result in a high piperazine conversation rate and a high selectivity for hydroxyethylpiperazine production at a commercial scale, e.g., relative to dihydroxyethylpiperazine (also referred to herewithin as DiHEP). Further, the continuous process will allow for continuous monitoring, with the option for adjustment in real time, of the ratio of ethylene oxide to piperazine in the reactor.

By continuous stirred tank reactor (also referred to herewithin and in the industry as CSTR) it is meant a tank reactor with an agitator that runs at steady state with continuous flow of reactants in and products out of the tank and continuous agitation. By plug flow reactor (as referred to hereinwithin and in the industry as PFR) it is meant a tubular reactor arranged as one long tube reactor or many short tube reactors that runs at steady state with continuous flow of reactants into an entrance of the tubular reactor and products out an exit of the tubular reactor (the exit end being at the opposite end of the tube as the entrance). The plug flow reactor may include flow obstructions.

By high piperazine conversation rate it is meant the conversation rate for piperazine is greater than 0.70 (e.g., greater than 0.75, greater than 0.80, greater than 0.85, greater than 0.90, greater than 0.95, greater than 0.96, etc.)

By high selectivity, it is meant the yield of moles of hydroxyethylpiperazine (in stream HEP Out) over moles of neat piperazine fed to a reactor (in stream PIP-IN in FIG. 1) is at least 50% and a yield of moles of dihydroxyethylpiperazine over moles of neat piperazine is less than 50%. For example, the yield of HEP may be from 55% to 100% (e.g., 60% to 100%, 65% to 100%, 60% to 99%, 60% to 95%, 65% to 85%, etc.) The yield of moles of DiHEP over moles of neat piperazine fed to a reactor (in stream Pip In) may be from 0% to 45% (e.g., 0% to 40%, 0% to 35%, 1% to 40%, 5% to 40%, 15% to 35%, etc.)

Figure 1:
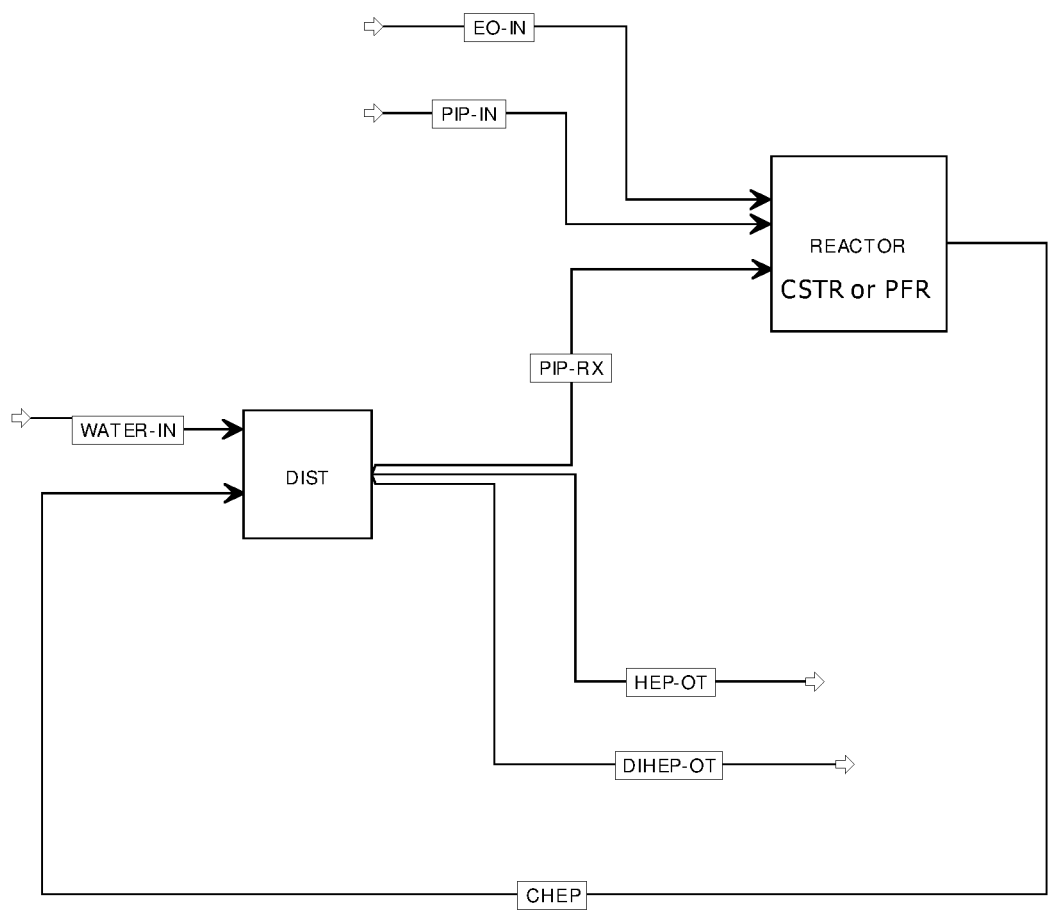
FIG. 1 illustrates a process flow diagram for an exemplary continuous reaction distillation process with a recycle stream for producing hydroxyethylpiperazine, for Working Examples 1 and 2.

Referring to FIG. 1, an exemplary process flow diagram is shown that utilizes continuous reaction (e.g., continuous feed of at least neat piperazine and recycled piperazine and optionally a continuous feed of ethylene oxide) with a distillation process to separate unreacted piperazine from a product stream to form the recycled piperazine. The process may further include adding a catalyst such as an ethoxylation catalyst (e.g., boron based catalysts).

In particular, as shown in FIG. 1, raw material continuous streams for ethylene oxide (EO-IN) and piperazine (PIP-IN) are fed to a continuous reactor (e.g., the continuous stirred tank reactor or the plug flow reactor). The reactor product, which is crude hydroxyethylpiperazine (CHEP), is a mixture that includes unreacted piperazine, hydroxyethylpiperazine, dihydroxyethylpiperazine, and water. The reactor product is continuously fed to a distillation system (DIST, e.g., that includes at least one distillation column) for a separation process. One of more water stream (WATER-IN) may be introduced to distillation system, e.g., for dilution of one or more streams and/or to adjust the freezing point of one or more streams. In the distillation system, at least three streams may be created. In particular, a hydroxyethylpiperazine product stream (HEP-OT), a dihydroxyethylpiperazine product stream (DIHEP-OT), and a recycled piperazine stream (PIP-RX). The hydroxyethylpiperazine product stream may be a final product stream and/or may be further processed to form a final product. The dihydroxyethylpiperazine product stream may be a final product stream, may be further processed to form a final product, and/or may be disposed. The recycled piperazine stream is fed back to the reactor, e.g., as a continuous feed of recycled piperazine to the reactor.

Figure 2:
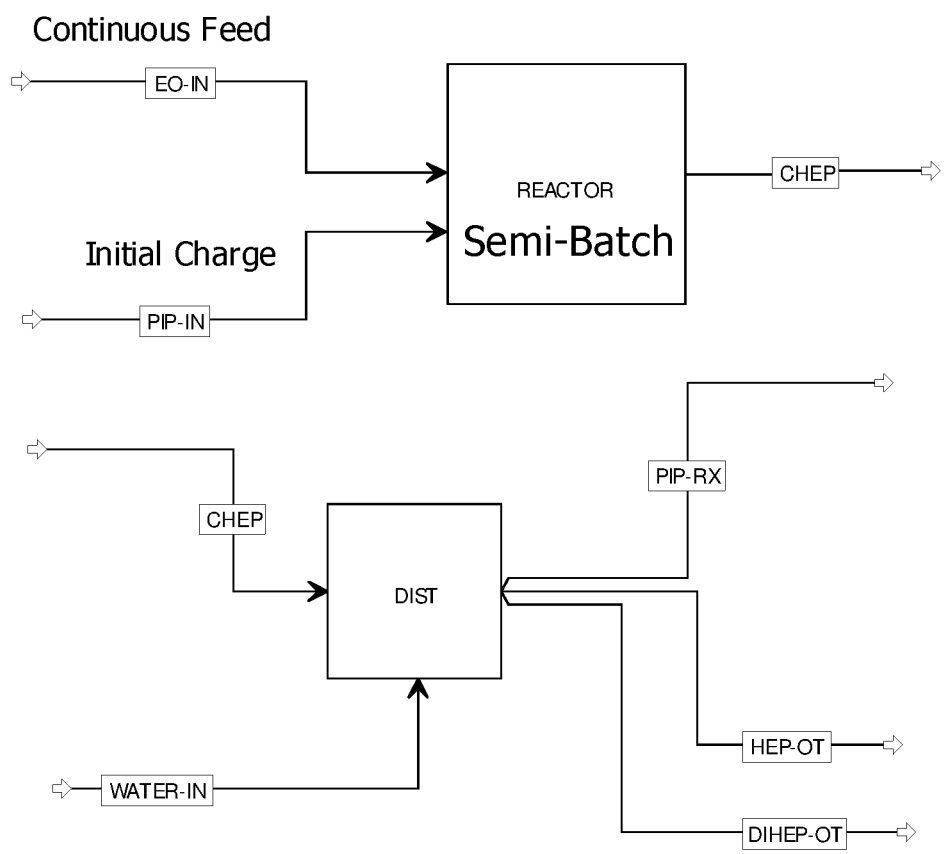
FIG. 2 illustrates a process flow diagram for a semi-batch reaction with distillation process without a recycle stream for producing hydroxyethylpiperazine, for Comparative Example A.

Referring to FIG. 2, a process flow diagram is shown that utilizes a comparative semi-batch reaction process with a distillation process. However, the unreacted piperazine from the distillation system is not recycled back to the semi-batch reactor. The semi-batch reactor receives an initial charge of piperazine in (PIP-IN) and a continuous feed of ethylene oxide (EO-IN) and after allowing the components to digest in the semi-batch reactor crude hydroxyethylpiperazine (CHEP) exists the reactor and is fed to a distillation system (DIST) for a separation process. A water stream (WATER-IN) may be introduced to distillation system. In the distillation system three streams are created. In particular, a hydroxyethylpiperazine product stream (HEP-OT), a dihydroxyethylpiperazine product stream (DIHEP-OT), and a piperazine stream (PIP-RX) that is not recycled back to the reactor. In particular, in this process the piperazine stream (PIP-RX) is not continuously feed back to the semi-batch reactor to aid in receiving high piperazine conversation rate and a high selectivity for hydroxyethylpiperazine production at a commercial scale.

Production System for Preparation of Hydroxyethylpiperazine

A continuous process for preparing hydroxyethylpiperazine may include (i) continuously feeding a stream of fresh piperazine into a reactor (e.g., continuous stirred tank or plug flow), (ii) continuously feeding a feed stream of ethylene oxide into the reactor, (iii) continuously feeding a stream of recycled piperazine into the reactor, (iv) continuously performing the reaction of piperazine and ethylene oxide in the reactor to form a crude hydroxyethylpiperazine product, (v) feeding the crude hydroxyethylpiperazine product to a distillation system that includes at least one distillation column, and (vi) producing in the distillation system a recycled piperazine stream. It is understood that by continuous it is meant a process in which the materials are being processed continuously for a period of time (e.g., for at least 1 hour), which is in contrast to a batch or semi-batch process where the materials are processed in stages.

The distillation system may include at least one distillation column. If two or more distillation columns are used, the distillation columns may be connected in series and/or parallel. If one distillation column is used, the distillation column may include multiple distillation sections that are arranged to operate similar to the theoretical use of two or more distillation columns with a theoretical top stream and bottom stream being produced in each section.

For example, when the distillation system includes two or more distillation sections/columns, a first distillation section/column may receive the crude hydroxyethylpiperazine product stream from the reactor. The first distillation section/column may produce a top stream that includes water and piperazine, which stream is then used to form the recycled piperazine to be fed back to the reactor. Further, the first distillation section/column may produce a bottom stream that includes hydroxyethylpiperazine and dihydroxyethylpiperazine. As such, in the first distillation section/column of the distillation system, the recycled piperazine stream may be separated before the dihydroxyethylpiperazine stream and the hydroxyethylpiperazine stream are separated from each other.

A second distillation section/column may receive the top stream of the first distillation section/column to separate water from the piperazine. A top stream of the second distillation section/column may include water and a bottom stream may include the piperazine to be used to form the recycled piperazine stream. The bottom stream of the second distillation section/column may be further adjusted outside of the distillation system to adjust the piperazine concentration before being fed back into the reactor. The top stream of the second distillation section/column may be waste water and/or may be further processed for use.

A third distillation section/column may receive the bottom stream of the first distillation section/column to separate hydroxyethylpiperazine from dihydroxyethylpiperazine. A top stream of the third distillation section/column may include hydroxyethylpiperazine and a bottom stream may include dihydroxyethylpiperazine. Further distillation sections/columns may be included in the distillation system, e.g., to further purify the recycled piperazine, hydroxyethylpiperazine and/or dihydroxyethylpiperazine product streams.

A hydroxyethylpiperazine product stream leaving the distillation system may have a HEP purity of at least 60 wt % (at least 70 wt %, at least 80 wt %, at least 90 wt %, at least 95 wt %, etc.). A dihydroxyethylpiperazine product stream leaving the distillations system may have a DiHEP purity of at least 35 wt % (at least 40 wt %, at least 50 wt %, at least 60 wt %, at least 70 wt %, at least 80 wt %, etc.) and optionally may be further diluted with one or more solvents.

A molar ratio of ethylene oxide to neat piperazine (from the fresh piperazine feed into the reactor) added to the reactor may be greater than 1.01 (e.g., greater than 1.02, greater than 1.05, greater than 1.10, greater than 1.15, greater than 1.20, greater than 1.22, etc.) The molar ratio of ethylene oxide to neat piperazine may be less than 4.00 (e.g., less than 3.50, less than 3.00, less than 2.50, less than 2.00, less than 1.99, less than 1.50, etc.) A molar ratio of ethylene oxide to total piperazine, including the neat piperazine and recycled piperazine added to the reactor may be less than 1.01 (less than 1.00, less than 0.90, less than 0.85, less than 0.80, less than 0.75, less than 0.70) and greater than 0.01 (e.g., greater than 0.05, greater than 0.10, greater than 0.20, greater than 0.30, greater than 0.40, greater than 0.50, greater than 0.60, etc.) For example, the molar ratio may be from 0.01 to 1.00.

The hydroxyethylpiperazine product stream from the distillation system includes at least 60 wt % hydroxyethylpiperazine based on a total weight of the hydroxyethylpiperazine stream. For example, from 60 wt % to 100 wt % (e.g., 65 wt % to 100 wt %, 70 wt % to 100 wt %, 80 wt % to 100 wt %, 85 wt % to 100 wt %, 90 wt % to 100 wt %, 95 wt % to 100 wt %, 97 wt % to 100 wt %, 98 wt % to 100 wt %, 99 wt % to 100 wt %, etc.) of hydroxyethylpiperazine, with a remainder being other components from crude hydroxyethylpiperazine.

The dihydroxyethylpiperazine product stream includes at least 35 wt % dihydroxyethylpiperazine based on a total weight of the dihydroxyethylpiperazine stream. For example, from 35 wt % to 100 wt % (e.g., 40 wt % to 100 wt %, 50 wt % to 100 wt %, 60 wt % to 100 wt %, 70 wt % to 100 wt %, 80 wt % to 100 wt %, 90 wt % to 100 wt %, 91 wt % to 100 wt %, etc.) of dihydroxyethylpiperazine, with a remainder being other components of crude hydroxyethylpiperazine. The dihydroxyethylpiperazine product stream may be further diluted with water after leaving the distillation system. The further diluted dihydroxyethylpiperazine product stream may include from 5 wt % to 80 wt % (e.g., 10 wt % to 70 wt %, 20 wt % to 60 wt %, 30 wt % to 55 wt %, 35 wt % to 50 wt %, 40 wt % to 45 wt %, etc.) of dihydroxyethylpiperazine.

A composition of the recycled piperazine stream may be adjusted, e.g., by adding or removing water, after leaving the distillation system and before being fed into the reactor as recycled piperazine. For example, the recycled piperazine stream may have a same or similar ratio of piperazine to solvent as the fresh piperazine feed into the reactor. For example, the fresh piperazine feed to the reactor may include from 30 wt % to 99 wt % (e.g., 40 wt % to 98 wt %, 50 wt % to 97 wt %, 55 wt % to 96 wt %, 60 wt % to 95 wt %, 50 wt % to 90 wt %, 60 wt % to 90 wt %, 50 wt % to 85 wt %, 60 wt % to 85 wt %, 50 wt % to 80 wt %, 60 wt % to 80 wt %, 50 wt % to 70 wt %, 60 wt % to 70 wt %, etc.) of piperazine in one or more solvents (e.g., at least water). Similarly, the recycled piperazine feed to the reactor may include from 30 wt % to 99 wt % (e.g., 40 wt % to 98 wt %, 50 wt % to 97 wt %, 55 wt % to 96 wt %, 60 wt % to 95 wt %, 50 wt % to 90 wt %, 60 wt % to 90 wt %, 50 wt % to 85 wt %, 60 wt % to 85 wt %, 50 wt % to 80 wt %, 60 wt % to 80 wt %, 50 wt % to 70 wt %, 60 wt % to 70 wt %, etc.) of piperazine in one or more solvents (e.g., at least water).

The reactants, such as the fresh piperazine and the ethylene oxide may be fed to the reactor near ambient temperature, e.g., from 20 to 25° C. The recycled piperazine may be cooled (e.g., from an initial temperature of greater than 80° C.) and fed to the reactor near ambient temperature, e.g., from 20 to 25° C. Further, the fresh piperazine, ethylene oxide, and recycled piperazine may be fed to the reactor at a pressure greater than atmospheric pressure, e.g., from 138 kPa to 689 kPa from 138 kPa to 552 kPa, from 207 kPa to 483 kPa, etc. The hydroxyethylpiperazine product stream may leave the distillation system at an elevated temperature, e.g., at a temperature greater than 60° C. (e.g., from 65° C. to 150° C., from 80° C. to 120° C., from 80° C. to 110° C., etc.).

Applications for Hydroxyethylpiperazine

Piperazine compounds have any number of practical applications including the production of plastics, resins and other industrial work products. Piperazines may also be used in various end use applications such as in enhanced oil and gas recovery, pesticides, automotive fluids, and pharmaceuticals. For example, hydroxyethylpiperazine may be used in the absorption of various contaminants often found in oil and gas streams. Exemplary contaminants include carbon dioxide, hydrogen sulfide, and other sulfur contaminants. For example, the hydroxyethylpiperazine may be used as a chemical solvent that absorbs the contaminants.

EXAMPLES

Approximate properties, characters, parameters, etc., are provided below with respect to the illustrative working examples, comparative examples, and the information used in the reported results for the working and comparative examples.

The following materials used include Ethylene Oxide (EO), Piperazine (PIP), and a Piperazine Solution that includes 68 wt % Piperazine and a remainder of water as a solvent with residual amounts of other impurities.

Working Examples 1 and 2 utilize a continuous reactor and a multicolumn distillation process with a recycle stream for producing hydroxyethylpiperazine, as shown in FIG. 1. Working Example 1 is based on use of a continuous stirred tank reactor (CSTR) and Working Example 2 is based on use of a plug flow reactor (PFR). Comparative Example A utilizes a conventional semi-batch reactor with multi-column distillation process without use of a recycle stream feed back to the semi-batch reactor for producing hydroxyethylpiperazine, as shown in FIG. 2.

Data in Table 1, below, is provided based on the amount of Neat Piperazine on a dry basis (i.e., excluding the water in feed as part of the Piperazine Solution) and assumes the Ethylene Oxide sample includes 100 wt % of EO. The HEP Product Stream, HEP-OT, as leaving the distillation system is assumed to have a purity of approximately 99.3 wt %, with the remainder being impurities. The DiHEP Product Stream, DIHEP-OT, is assumed to have a purity of approximately 43.7 wt %, with the remainder being water and impurities. For the simulation the DiHEP Product Stream is assumed to be diluted in water to the 43.7 wt % purity, in practice the water for dilution may be added to the DiHEP Product Stream after exiting the distillation system. Table 1 data is based on producing the same amount of HEP product (i.e. 47.6 Mlb), assuming distillation systems are the same for the three examples.

Piperazine conversion is measured as the conversion of Piperazine based on the feed of Neat Piperazine, without including the recycled Piperazine. With respect to product yield, HEP yield is defined as moles of HEP produced over moles of Piperazine fed to the reactor. Further, DiHEP Yield is defined as moles of DiHEP produced over moles of Piperazine fed to the reactor. Overall Molar Selectivity HEP to DiHEP is the moles of produced HEP over moles of produced DiHEP.

TABLE 1

|  | Working Example 1 | Working Example 2 | Comparative Example A |
|---|---|---|---|
| Feed (tonnes) | | | |
| Ethylene Oxide | 13.2 | 9.7 | 13.2 |
| Neat Piperazine | 20.4 | 16.9 | 28.1 |
| Molar Ratio to Reactor | | | |
| Ethylene Oxide to Neat Piperazine Molar Ratio* (without recycle stream) | 1.37 | 1.23 | 1.01 |
| Ethylene Oxide to Total Neat Piperazine Molar Ratio (with recycle stream) | 0.67 | 0.61 | 1.01 |
| Product (tonnes) | | | |
| HEP Product Stream (HEP-OT) (~99.3 wt % purity) | 21.6 | 21.6 | 21.6 |
| DiHEP Product Stream (DIHEP-OT) (~43.7 wt % purity)** | 25.2 | 10.5 | 24.41 |
| Piperazine Conversion | | | |
| Conversion Rate | 0.97 | 0.98 | 0.70 |
| Overall Yield (product streams) | | | |
| HEP (%) | 69.9 | 84.7 | 50.9 |
| DiHEP (%) | 38.1 | 15.8 | 36.9 |
| Molar Selectivity | | | |
| HEP to DiHEP | 2.6 | 6.3 | 2.7 |

*based on total moles of neat piperazine on a dry basis, without including recycled piperazine.
**the 43.7 wt % purity is based on dilution of the resultant DiHEP Product Stream with water Referring to Table 1, it shown that use of the recycle piperazine stream may allow for a lower feed requirement for the Neat Piperazine without compromising purity for the HEP Product Stream, while unexpectedly resulting in a higher piperazine conversation rate and overall yield for HEP product streams. Further, with respect to Working Example 1, it is found that use of the CSTR with the recycle stream may allow for significant improvements for overall yield and comparable HEP to DiHEP selectivity relative to the conventional semi-batch process in Comparative Example A. With respect to Working Example 2, it is found that use of the PFR may allow for significant improvements for both overall yield and HEP to DiHEP selectivity and overall yield relative to both conventional semi-batch process in Comparative Example and the CSTR reactor of Working Example 1.

The data for Table 1 is prepared using a commercially available simulation software, ASPENPLUS™ version 8.6 (available from Aspen Technology). Physical properties are developed from data regression. Reactor module Plug (for PFR reactor), RCSTR (for CSTR reactor), and rigorous distillation module RADFRAC are used within Aspen. The distillation process includes multi columns. Each column is sufficiently staged with either trays or packing to achieve desired product separation purity. The operation pressure could be under vacuum. For the examples, the following three columns are included in the distillation process:

1) a 17 stage unit under vacuum (51 kPa) is configured to separate PIP and water from reaction crude,
2) a 17 stage unit under deep vacuum (0.5 kPa) is configured for HEP separation from DIHEP, and
3) a 12 stage unit under atmospheric pressure is configured for PIP separation.

The distillation system is usually limited by the reboiler duty of the first column with top temperature controlled at 110° C. In order to produce the same amount of HEP of desired purity, the raw materials, conversion, product yield and selectivity are compared for the examples. In all the examples, distillation duty remains the same for the first column at 1.52 kJ/hr for a fair comparison. The streams from Aspen model are reported in Table 2, Table 3, and Table 4, for respective Working Examples 1 and 2 and Comparative Example A.

For Working Examples 1 and 2 the parameters used in the simulation are below in Tables 2 and 3, respectively. Referring to Tables 2 and 3, EO In refers to the Ethylene Oxide feed into the reactor and PIP refers to the Neat Piperazine feed into the reactor. PIP Rx refers to the recycled piperazine stream that has been diluted with water to have a concentration of approximately 68 wt % of Piperazine, such that it is the stream as it enters the reactor. HEP Out refers to the hydroxyethylpiperazine stream out of the distillation system having a purity of greater than 99 wt %. DiHEP Out refers to the dihydroxyethylpiperazine stream out of the distillation system as diluted with water to have a 43.7 wt % purity. HEP Out pressure refers to the pressure of the distillation column that separates hydroxyethylpiperazine from dihydroxyethylpiperazine. DiHEP Out pressure refers to the pressure the DiHEP stream is pumped up to prior to dilution to 43.7% purity.

TABLE 2

|  | EO-IN | PIP-IN | PIP-RX | HEP-OT | DiHEP-OT |
|---|---|---|---|---|---|
| Molar Flow (kmol/hr) | | | | | |
| Water | 0 | 7.18 | 7.95 | <0.01 | 9.87 |
| Neat Piperazine | 0 | 3.19 | 3.38 | 0.02 | <0.01 |
| REP | 0 | 0 | 0.02 | 2.22 | 0.10 |
| DiHEP | 0 | 0 | <0.01 | <0.01 | 0.85 |
| Ethylene Oxide | 4.02 | 0 | 0 | 0 | 0 |
| Mass Flow (kg/hr) | | | | | |
| Water | 0 | 129.29 | 143.16 | <0.01 | 177.80 |
| Neat Piperazine | 0 | 247.75 | 291.13 | 1.87 | <0.01 |
| REP | 0 | 0 | 3.00 | 288.51 | 12.87 |
| DiHEP | 0 | 0 | 0.06 | 0.03 | 148.00 |
| Ethylene Oxide | 176.90 | 0 | 0 | 0 | 0 |
| Mass Frac | | | | | |
| Water | 0 | 0.32 | 0.33 | <0.01 | 0.53 |
| Neat Piperazine | 0 | 0.68 | 0.66 | 0.01 | <0.01 |
| REP | 0 | 0 | 0.01 | 0.99 | 0.04 |
| DiHEP | 0 | 0 | <0.01 | <0.01 | 0.44 |
| Ethylene Oxide | 1.00 | 0 | 0 | 0 | 0 |
| Totals | | | | | |
| Total Flow (kmol/hr) | 4.02 | 10.37 | 11.35 | 2.24 | 10.82 |
| Total Flow (kg/hr) | 176.90 | 404.05 | 437.35 | 290.41 | 338.68 |
| Total flow (m³/hr) | 0.20 | 0.39 | 0.45 | 0.29 | 0.33 |

TABLE 2-continued

| | EO-IN | PIP-IN | PIP-RX | HEP-OT | DiHEP-OT |
|---|---|---|---|---|---|
| Temperature (° C.) | | | | | |
| | 20.0 | 20.0 | 96.8 | 92.3 | 67.0 |
| Pressure (kPa) | | | | | |
| | 330.9 | 330.9 | 330.9 | 0.4 | 101.3 |

For Working Example 2, the parameters used in the simulation are below in Table 3.

TABLE 3

| | EO-IN | PIP-IN | PIP-RX | HEP-OT | DiHEP-OT |
|---|---|---|---|---|---|
| Molar Flow (kmol/hr) | | | | | |
| Water | 0 | 7.43 | 7.84 | <0.01 | 5.15 |
| Neat Piperazine | 0 | 3.30 | 3.40 | 0.03 | <0.01 |
| REP | 0 | 0 | 0.03 | 2.78 | 0.05 |
| DiHEP | 0 | 0 | <0.01 | <0.01 | 0.44 |
| Ethylene Oxide | 3.72 | 0 | 0 | 0 | 0 |
| Mass Flow (kg/hr) | | | | | |
| Water | 0 | 133.89 | 141.21 | <0.01 | 92.70 |
| Neat Piperazine | 0 | 284.52 | 292.93 | 2.16 | <0.01 |
| REP | 0 | 0 | 3.63 | 361.86 | 6.71 |
| DiHEP | 0 | 0 | 0.03 | 0.04 | 77.16 |
| Ethylene Oxide | 163.75 | 0 | 0 | 0 | 0 |
| Mass Frac | | | | | |
| Water | 0 | 0.32 | 0.32 | <0.01 | 0.52 |
| Neat Piperazine | 0 | 0.68 | 0.67 | 0.01 | <0.01 |
| REP | 0 | 0 | <0.01 | 0.99 | 0.04 |
| DiHEP | 0 | 0 | <0.01 | <0.01 | 0.44 |
| Ethylene Oxide | 1.00 | 0 | 0 | 0 | 0 |
| Totals | | | | | |
| Total Flow (kmol/hr) | 3.72 | 10.74 | 11.27 | 2.80 | 5.64 |
| Total Flow (kg/hr) | 163.75 | 418.41 | 437.80 | 364.06 | 176.57 |
| Total flow (m³/hr) | 0.19 | 0.40 | 0.45 | 0.36 | 0.17 |
| Temperature (° C.) | | | | | |
| | 20.0 | 20.0 | 97.4 | 92.7 | 67.6 |
| Pressure (kPa) | | | | | |
| | 330.9 | 330.9 | 330.9 | 0.4 | 101.3 |

For Comparative Example A, the parameters used in the simulation are below in Table 4. CHEP Out refers to the crude hydroxyethylpiperazine stream leaving the reactor and entering the distillation system. PIP Rx refers to the Piperazine stream that leaves the distillation system, which for Comparative Example A is not recycled back to the reactor. HEP Out refers to the hydroxyethylpiperazine stream out of the distillation system and DiHEP Out refers to the dihydroxyethylpiperazine stream out of the distillation system as diluted with water to have a 43.7 wt % purity.

TABLE 4

| | CHEP* | PIP-RX | HEP-OT | DiHEP-OT |
|---|---|---|---|---|
| Molar Flow (kmol/hr) | | | | |
| Water | 14.16 | 4.02 | 0 | 13.74 |
| Neat Piperazine | 1.71 | 1.71 | <0.01 | <0.01 |
| HEP | 3.40 | 0.05 | 3.21 | 0.14 |
| DiHEP | 1.18 | <0.01 | <0.01 | 1.18 |
| Mass Flow (kg/hr) | | | | |
| Water | 255.14 | 72.34 | 0 | 247.57 |
| Neat Piperazine | 147.29 | 146.99 | <0.01 | <0.01 |
| HEP | 442.77 | 7.07 | 417.79 | 17.92 |
| DiHEP | 206.20 | 0.09 | 0.04 | 206.07 |
| Mass Frac | | | | |
| Water | 0.24 | 0.32 | <0.01 | 0.52 |
| Neat Piperazine | 0.14 | 0.65 | <0.01 | <0.01 |
| HEP | 0.42 | 0.03 | 0.99 | 0.04 |
| DiHEP | 0.20 | <0.01 | <0.01 | 0.44 |
| Totals | | | | |
| Total Flow (kmol/hr) | 20.46 | 5.78 | 3.21 | 15.06 |
| Total Flow (kg/hr) | 1051.41 | 226.48 | 417.83 | 471.56 |
| Total flow (m³/hr) | 0.99 | 0.23 | 0.41 | 0.46 |
| Temperature (° C.) | | | | |
| | 60.0 | 98.1 | 96.9 | 68.4 |
| Pressure (kPa) | | | | |
| | 273.7 | 102.7 | 0.4 | 101.3 |

*The CHEP stream composition is measured as the outlet from the Semibatch Reactor Further, for Comparative Example A the semibatch reaction parameters used in the simulation are below in Table 5.

TABLE 5

| Neat Piperazine (kg) | 28068 |
|---|---|
| EO (kg) | 13154 |
| Semibatch time (hr) | 2.5 |
| CHEP Product (kg) | 54431 |

The invention claimed is:

1. A continuous process for the production of hydroxyethylpiperazine, the process comprising:
    feeding neat piperazine, recycled piperazine, and ethylene oxide to a reactor to form crude hydroxyethylpiperazine, the reactor being a continuous stirred tank reactor or a plug flow reactor, wherein a molar ratio of ethylene oxide to neat piperazine added to the reactor is greater than 1.01; and
    continuously feeding the crude hydroxyethylpiperazine from the reactor to a distillation system that includes at least one distillation column, the distillation system producing at least a recycled piperazine stream and a hydroxyethylpiperazine stream, the recycled piperazine stream including the recycled piperazine that is fed to the reactor to form the crude hydroxyethylpiperazine and the hydroxyethylpiperazine stream including at least 60 wt % of hydroxyethylpiperazine based on a total weight of the hydroxyethylpiperazine stream.

2. The process as claimed in claim 1, wherein a molar ratio of ethylene oxide to total piperazine, including neat piperazine and recycled piperazine, is from 0.10 to 1.01.

3. The process as claimed in claim 1, wherein the recycled piperazine stream includes from 30 wt % to 99 wt % of piperazine.

4. The process as claimed in claim 1, wherein the distillation system includes three distillation columns, a first distillation column receives the crude hydroxyethylpiperazine from the reactor, a second distillation column receives a top stream of the first distillation column and separates water from piperazine, and a third distillation column receives a bottom stream from the first distillation column and separates hydroxyethylpiperazine from dihydroxyethylpiperazine.

5. The process as claimed in claim 1, wherein the distillation system further produces a dihydroxyethylpiperazine stream that includes at least 35 wt % dihydroxyethylpiperazine based on a total weight of the dihydroxyethylpiperazine stream.

6. The process as claimed in claim 5, wherein in the distillation system the recycled piperazine stream is separated first before the dihydroxyethylpiperazine stream and the hydroxyethylpiperazine stream are separated from each other.

7. The process as claimed in claim 1, wherein the recycled piperazine stream diluted with water is continuously fed directly to the reactor.

8. The process of claims in claim 1, wherein the reactor is a plug flow reactor.

* * * * *